(12) United States Patent
Rohr et al.

(10) Patent No.: US 7,108,680 B2
(45) Date of Patent: Sep. 19, 2006

(54) CLOSED-LOOP DRUG DELIVERY SYSTEM

(75) Inventors: William L. Rohr, Marshfield, MA (US); Alan J. Dextradeur, Franklin, MA (US); David D. Konieczynski, Needham, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 209 days.

(21) Appl. No.: 10/092,955

(22) Filed: Mar. 6, 2002

(65) Prior Publication Data

US 2003/0171711 A1   Sep. 11, 2003

(51) Int. Cl.
*A61M 1/00* (2006.01)
*A61M 31/00* (2006.01)

(52) U.S. Cl. .......................................... 604/151; 604/65

(58) Field of Classification Search ................ 600/347, 600/365–345, 323; 607/60, 22; 604/151, 604/43, 93.01, 65–67
See application file for complete search history.

(56) References Cited

U.S. PATENT DOCUMENTS

| | | | |
|---|---|---|---|
| 4,146,029 A * | 3/1979 | Ellinwood, Jr. ........... | 604/891.1 |
| 4,889,407 A | 12/1989 | Markle et al. | |
| 5,305,745 A | 4/1994 | Zacouto | |
| 5,474,552 A | 12/1995 | Palti | |
| 5,511,547 A | 4/1996 | Markle et al. | |
| 5,596,988 A | 1/1997 | Markle et al. | |
| 5,676,145 A | 10/1997 | Bar-Lavie | |
| 5,697,899 A | 12/1997 | Hillman et al. | |
| 5,700,897 A | 12/1997 | Klainer et al. | |
| 5,711,315 A | 1/1998 | Jerusalmy | |
| 5,711,316 A | 1/1998 | Elsberry et al. | |
| 5,720,720 A | 2/1998 | Laske et al. | |
| 5,730,125 A | 3/1998 | Prutchi et al. | |
| 5,730,714 A | 3/1998 | Guy et al. | |
| 5,735,814 A | 4/1998 | Elsberry et al. | |
| 5,782,798 A | 7/1998 | Rise | |
| 5,792,212 A | 8/1998 | Weijand | |

(Continued)

FOREIGN PATENT DOCUMENTS

EP       1048264       11/2000

(Continued)

OTHER PUBLICATIONS

R.R. Lonser et al., *Direct Convective Delivery Of Macromolecules To The Spinal Cord*, J. Neurosurg, 89:616-622 (1998).

(Continued)

*Primary Examiner*—Sharon Kennedy
(74) *Attorney, Agent, or Firm*—Nutter, McClennen & Fish LLP

(57) ABSTRACT

A delivery system for a drug or bioactive agent includes an implantable pump and a delivery conduit that may be implanted in an organ or other tissue (e.g., the central or the peripheral nervous system) of a subject. A sensor is also implanted, and a controller unit receives the sensor output and directs drug delivery from within the patient pump accordingly. The sensor directly measures a primary biochemical material or state in the tissue or organ system, and the monitoring unit effects closed loop feedback control of the pump to achieve a desired end. The end may be the regulation of metabolism or maintenance of a stable metabolic or other state, or may be treatment regimen, e.g., by delivery of a dosage level or distribution of a drug in specific brain or nervous an system tissue. The sensed material may be the agent itself, a metabolite, or a related native material, tissue state or condition.

18 Claims, 3 Drawing Sheets

U.S. PATENT DOCUMENTS

| | | | |
|---|---|---|---|
| 5,797,898 | A | 8/1998 | Santini, Jr. et al. |
| 5,820,622 | A | 10/1998 | Gross et al. |
| 5,978,702 | A | 11/1999 | Ward et al. |
| 6,016,449 | A | 1/2000 | Fischell et al. |
| 6,032,059 | A | 2/2000 | Henning et al. |
| 6,122,536 | A | 9/2000 | Sun et al. |
| 6,175,752 | B1 | 1/2001 | Say et al. |
| 6,263,237 | B1 * | 7/2001 | Rise .............................. 607/3 |
| 6,442,413 | B1 * | 8/2002 | Silver |
| 6,464,687 | B1 * | 10/2002 | Ishikawa et al. ......... 604/891.1 |
| 6,501,983 | B1 * | 12/2002 | Natarajan et al. ........... 600/517 |
| 6,558,351 | B1 * | 5/2003 | Steil et al. .................. 604/131 |
| 2002/0138018 | A1 * | 9/2002 | Lange et al. |

FOREIGN PATENT DOCUMENTS

| | | |
|---|---|---|
| WO | WO 02/11703 A1 | 2/2002 |

OTHER PUBLICATIONS

M.Y. Chen et al., *Variables Affecting Convection-Enhanced Delivery To The Striatum: A Systematic Examination Of Rate Of Infusion, Cannula Size, Infusate Concentration, and Tissue-Cannula Sealing Time*, J. Neurosurg, 90:315-320 (1999).

J.W. McDonald et al., *Repairing The Damaged Spinal Cord*, Scientific American, p. 65-73 (Sep. 1999).

R. F. Service, *Drug Deliver: Silicon Chips Find Role As In Vivo Pharmacist*, News of the Week, 283:619 (Jan. 29, 1999).

M. Larkin, *"Pharmacy" On A Microchip Looks Promising*, The Lancet, 353:385 (Jan. 30, 1999).

S. Borman, *Microchips Deliver On Command*, C&EN, pp. 30 and 31 (Feb. 1, 1999).

D.N. Leff, *Dime-Size, Programmable Drug-Delivery Microchip Passes Proof-of-Principle Test*, Bio World Today, 10:18:1,3 (Jan. 28, 1999).

D. Stover, *Pharmacy On A Chip*, Popular Science, p. 33 (Apr. 1999).

J. O'Neil, *Implantable Chip Offers Hope Of Simplifying Drug Regimens*, Health & Fitness, N.Y. Times, Feb. 2, 1999, at D6 (NE).

J. T. Santini, Jr., et al, *A Controlled-Release Microchip*, Nature, 394, 335-338, (Jan. 28, 1999).

\* cited by examiner

CLOSED-LOOP DRUG DELIVERY SYSTEM

FIELD OF THE INVENTION

This invention pertains to the delivery of pharmaceutical or bioactive material (hereafter called simply "a drug") to tissue or organ sites of a subject. Specifically, this invention relates to an implantable and controlled drug delivery system having a closed loop feedback control system.

BACKGROUND OF THE INVENTION

Many infusion pumps are known, both with programmable control regimens and with preset or even structurally-fixed delivery characteristics. In practice, a decision to medicate a patient typically results from testing and diagnosis, and involves a decision on dosage, often together with actions to monitor the effects of medication, or the symptomatic need for further or continued medication. The target condition may be such that monitoring is necessary only at intervals of days, weeks or longer. In other cases, a medication may be administered prophylactically, before detection of a symptom, or it may be administered belatedly, when symptomatic secondary effects have been observed and the medication can, at best, limit further damage. In some circumstances, monitoring may also be required to detect the occurrence of a specific side effect or adverse reaction.

A drug delivery system typically includes an infusion pump, for example, having a housing which contains a fluid pump and a drug chamber. The pump may be implanted subdermally, with a local outlet, or with a delivery (infusion) catheter extending from the pump to an intended drug delivery site in target tissue. Thus, such a system can be partly or wholly implanted within an individual. The infusion catheter, if one is provided, is routed so as to deliver the drug to a target site within a subject. To operate the drug delivery system, the fluid pump is activated, which may be set based on expected conditions, and which regulates the duration, flow rate or other parameters of drug delivery. Once the fluid pump is activated, fluid moves along the delivery catheter toward the target site, and is released at the target site.

Certain closed-loop feedback control drug delivery systems are known and are employed for monitoring and treating disorders of the CNS. Such systems often employ sensors that detect electric activity resulting from some patho-physiological event. For example, U.S. Pat. No. 5,735,814 discloses a closed-loop system comprising multiple sensor electrodes for treating neurological diseases. This system employs electrodes which are placed in close proximity to the brain or deep within brain tissue in order to detect a secondary event such as electrical activity that is produced in response to some neurological event. The electrodes can detect the electrical activity resulting from the neurological event, e.g., the electrical activity following an ischemic event in the CNS. A signal from the monitoring system is then communicated to a control unit. The control unit will process the information and then initiate a response in order to terminate the undesirable neurological event, e.g., the release and delivery of one or more drugs from an infusion pump system.

Methods for treating neurodegenerative disorders like Parkinson's disease have been described, for example, in U.S. Pat. Nos. 5,711,315 and 6,016,449. Some methods include an infusion pump implanted within the affected individual. Along with the infusion pump, a monitoring system is also employed. Sensors placed within the brain detect aberrant electrical activity and communicate with a microprocessor which, in turn, regulates the infusion pump. Drugs housed within the infusion pump are released into certain brain areas in response to a signal sent from the microprocessor.

One concern regarding these systems is that by relying upon the detection of secondary phenomena, such as the electrical activity, rather than the primary phenomena, response time and therapeutic precision may be compromised.

Accordingly, there currently exists a need for an implantable closed-loop feedback drug delivery system which includes a monitoring system capable of directly measuring a primary biochemical parameter which underlies a particular disorder, and responding rapidly to the detected biochemical parameter with an appropriate drug treatment.

SUMMARY OF THE INVENTION

The present invention provides a drug delivery system that is effective, on a real time basis, to assess primary biochemical parameters and/or events and to deliver one or more drugs to a tissue site, virtually instantaneously, to respond to the detected biochemical parameter. The invention is thus an improved closed-loop feedback control system that is particularly advantageous in the treatment of disorders of the central nervous system. Patient safety and well-being are enhanced not only by obviating the need to expose the patient to electrical circuitry, but also by providing an enhanced therapeutic response to sensed biochemical events.

The invention provides a significant advantage in that biologic processes that give rise to treatments involving the system of the invention are dynamic; they vary from individual to individual, disease to disease. The need for a particular drug or biological agent, and the dose of the agent required, will also vary with changing severity of a disease. For example, as a patient's health improves, the drug or biological agent may be metabolized at a faster rate, so a higher dose would be required. The closed-loop, biological feedback sensor-based system of the invention enables a rapid response to be made based on a patient's changing needs.

The closed-loop feedback control system of the present invention provides a delivery system that is at least partly implantable within a subject. The system includes a drug delivery device, a delivery conduit, one or more biosensors, and a controller unit that may be associated with the drug delivery device. Preferably all components of the system are implanted within a tissue or organ site within a subject's body. In one embodiment the distal or delivery end of the delivery conduit is disposed within tissue of the central or peripheral nervous system and the biosensor(s) is disposed in the same tissue or organ system or within another tissue or organ system of the patient. The biosensor(s) can be disposed local to or remote from the delivery end of the delivery conduit. In operation the system monitors one or more biochemical events or parameters and, based on the sensed data, controls the delivery parameters (e.g., flow rate and duration) of one or more drugs housed within the drug delivery device. That is, the biosensor(s) detects a biochemical event or parameter and conveys a signal representative of the sensed data to the controller unit. Based on this information, and any pre-programmed or subsequently programmed operating procedures, the controller unit then instructs the drug delivery device (e.g., infusion pump) to deliver one or more drugs at an appropriate flow rate and for an appropriate duration to maintain the sensed parameters within a predetermined, acceptable range. The biosensor(s) continuously monitor the subject to make any adjustments to the drug delivery parameters to maintain the parameters within a predetermined, acceptable range. The sensed parameters can give the physician critical information on the subject's disease state, thus enabling the dosage requirement to be established. The physician can control the drug delivery parameters, and make any future adjustments, based on the information generated by the biosensor(s).

The sensed biochemical parameters or events preferably include events that are directly related to an underlying medical condition or disorder. The biosensor(s) may thus detect the presence and/or concentration of one or more infused drugs, or the presence and/or concentration of metabolites or physiologic chemicals that derive from the administration of such drugs. Further, the biosensor(s) may detect pH, a chemical, an ion, a biological molecule, a gas, spectral indicators thereof, and combinations thereof.

The biosensor(s) may be placed in the same tissue or organ as the distal (delivery) end of the delivery conduit. Alternatively, the biosensor(s) may be placed within another tissue or organ system to monitor an event or biochemical compound that results from the drug treatment. Biosensor(s) implanted in the same tissue but at a distance from the delivery catheter may be used to develop indications of intra-tissue distribution of a neurochemical, such as dopamine or acetylcholine, or of the delivered drug itself, while a sensor more remote from the delivery catheter may monitor the amount of drug present locally (e.g., in CSF or the intrathecal space), or it may detect a metabolite or other drug or condition-indicator locally or systemically. For example, the biosensor(s) may detect an indicator of cellular metabolism, such as a material or enzyme involved in energy production at the cellular level, or it may detect a metabolite, e.g., a metabolite of the delivered drug. Alternatively, the biosensor(s) may monitor the dopamine/acetylcholine balance and control delivery, e.g., of Levadopa, to correct a dopamine deficiency, or the biosensor(s) may if provide feedback data to enable the control unit to deliver another drug based on a measured or modeled clearance rate in order to accurately achieve a desired state, set point or distribution. The biosensor(s) may also detect physiologic chemistry, such as pH or an electrolyte concentration, to provide a local or an immediate and primary indicator for drug initiation. In some embodiments the biosensor(s) may detect a systemic material or parameter for controlling the drug delivery parameters.

In a further embodiment, the delivery conduit is implanted to deliver a drug to a portion of the central nervous system, such as the parenchyma of the brain, and the sensor is implanted at a site most appropriate for the intended application. For example, in trauma cases it is generally desirable to place the sensor at a site peripheral to the delivery site, while in the treatment of certain diseases (e.g., epilepsy) it is desireable to place the sensor at a site local to the delivery site.

One embodiment seeks to prevent ischemic damage of central or peripheral nervous system tissue consequent to trauma, and employs fiber-based biosensor(s) capable of substantially continuous polling detection with minimal disruption of the surrounding biological processes. The biosensor(s) provide immediate detection of one or multiple parameters, allowing the control unit to initiate intervention in cases of trauma, or to adjust or discontinue a treatment before the complexity of metabolic disruption has led to damage or irreversible processes. Another embodiment may manage chronic or acute pain by localized administration of a highly concentrated morphine-like pain killer in nervous system tissue. Yet another embodiment may administer material such as a hormone in a cyclic or varying regimen, with the closed loop feedback serving to adjust delivery, with suitable lag or lead times, to maintain a temporally-varying set point. Still another embodiment may detect levels of neurotransmitter or other neurochemical agents, and administer material to control or ameliorate effects of Parkinson's disease or other neurologic or neurodegenerative diseases.

Systems of the invention may also be utilized for investigative purposes, such as gathering data to determine the functional relationship between the delivery of drugs and the level or presence of a sensed spectral component, or their effects on a process, metabolite or substance of interest in the nervous system. In addition to sensing a local state, a system of the invention may also utilize biosensor(s) positioned to sense a regional or global effect, and to detect or monitor one or more potential side effects or diagnostic indicia.

BRIEF DESCRIPTION OF THE DRAWINGS

These and other aspects of the invention will be understood from the description below and the appended claims, taken together with the figures showing illustrative embodiments, wherein:

DETAILED DESCRIPTION OF THE INVENTION

Figure 1:
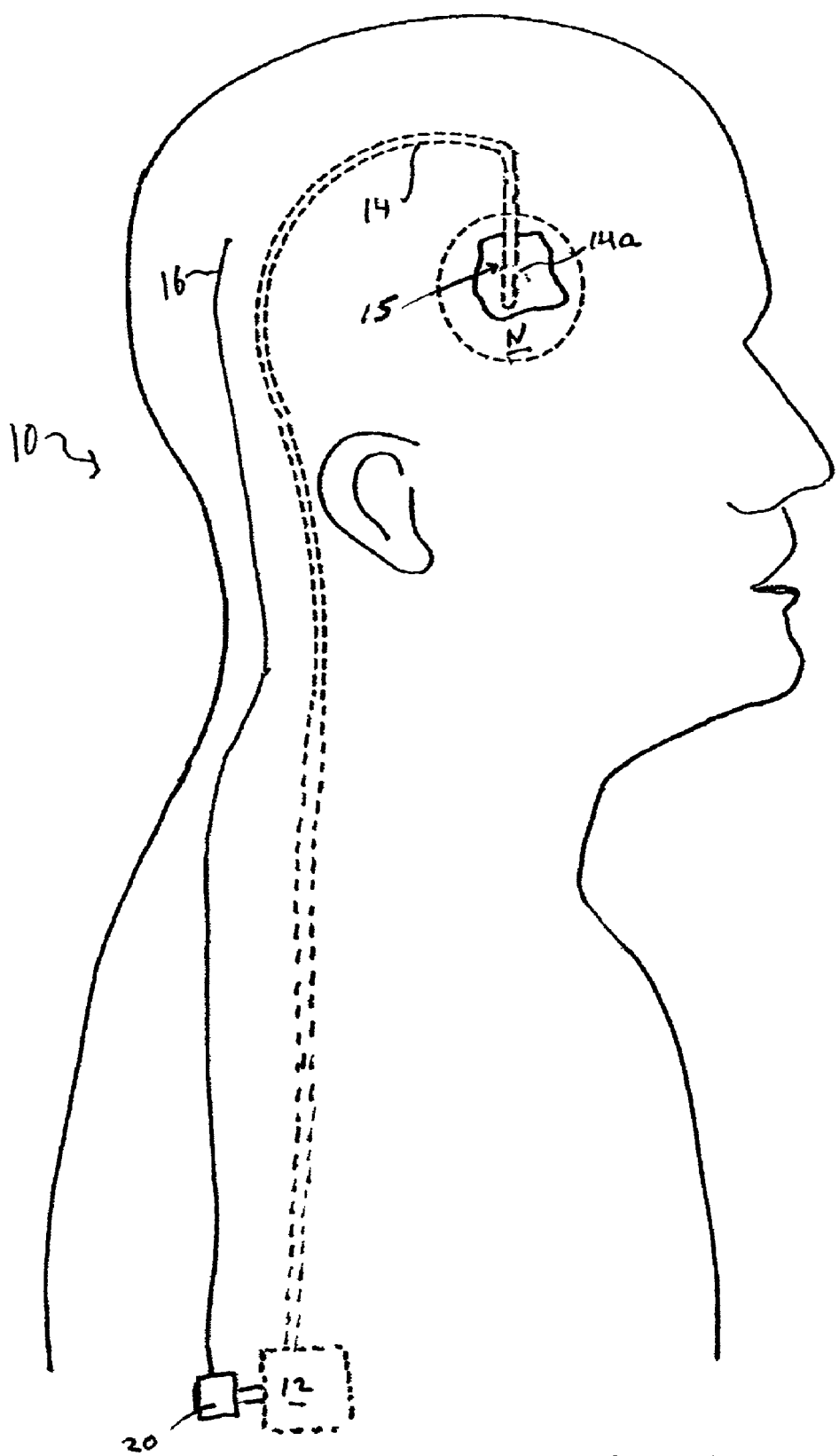
FIG. 1 schematically illustrates a system of the present invention.

FIG. 1 schematically illustrates a system 10 in accordance with the present invention. An implantable controlled drug release or pump unit 12 is in fluid communication with an implanted delivery conduit 14 having one or more ports or pore regions 14a located at a distal delivery end 15. The system also includes one or more biosensor(s) 16 that communicate with a controller unit 20 that either forms part of the pump unit 12 or is in communication with the pump unit. The pump unit 12 contains one or more chambers (not shown) for housing one or more drugs to be delivered through the delivery conduit 14 to a tissue site or organ within a subject.

As noted above, the entire system 10 is preferably adapted to be implanted within a subject. In one embodiment the distal delivery end 15 is positioned within patient tissue to which the drug(s) is to be delivered. For example, the delivery end 15 can be disposed within tissue of the nervous system N of a subject, so that a drug or biological treatment material is locally delivered directly to such tissue. The biosensor(s) 16 are also adapted to be positioned in patient tissue to detect one or more biochemical parameters or events. The biosensor(s) may be placed within the same tissue or organ system (e.g., the nervous system) as the delivery end 15. Alternatively, the biosensor(s) may be placed within another tissue system or organ. Moreover, the biosensor(s) may be placed local to or remote from the delivery end 15.

The pump unit 12 may be of any conventional type, including a diaphragm-type or peristaltic-type infusion pump, or a pressurized reservoir having known or modeled delivery characteristics. The flow rate may be preset or based upon known or modeled properties (such as tissue permeability, drug and fluid viscosity, drug clearance rate, catheter and outlet port dimensions, and the like). Alternatively, the flow rate may be based on an empirically accepted delivery rate calculated to achieve a desired tissue concentration of the drug. Preferably, however, the pump flow rate is adjustable and is able to be adjusted based upon one or more extrinsic inputs, such as the data that the controller unit 20 receives from the biosensor(s) 16.

The delivery conduit 14 may be a catheter of any known type that is capable of being implanted within a subject for an extended period of time and capable of delivering fluid from the pump unit to a desired site. Exemplary delivery conduits include needles, catheters, and porous fibers or catheters. The dimensions and properties of the delivery conduit will vary based upon the requirements of a given patient and the medical condition to be treated. One of ordinary skill in the art will readily be able to determine an acceptable delivery conduit for use with the present invention.

The biosensor(s) 16 should be of a type such that they are able to achieve the direct, real-time monitoring of subcellular processes in conjunction with a closed loop drug delivery system. Such biosensors should be effective to monitor the concentration of intracellular analytes, such as proteins, enzymes, antibodies, neurotransmitters and neuropeptides, as well as their time developments, individually or simultaneously. One of ordinary skill in the art will appreciate that a variety of such sensors are known to exist and currently are used in medical diagnostics that require detection of small molecules (e.g., antibiotics) at very low concentration levels.

Biosensors are particularly advantageous since they offer the ability to achieve simultaneous detection of several analytes present at low concentrations in a tissue. Further, biochemical sensors offer significant advantages in terms of the speed and ease of the assay, as well as the possibility to detect a number of different analytes. Among the more preferred types of biosensors are integrated optical (IO), which offer the advantages of being small and very sensitive.

A variety of optically-based biosensors are known. These include IO sensors that utilize fluorescent or luminescent indicators, chromogenic indicators, absorption indicators, and temperature or pressure sensitive indicators. Fluorescence-based IO systems are particularly well-suited to detecting low molecular weight analytes. Examples of useful biosensors are disclosed in European Patent No. EP 745 220 B1, and in U.S. Pat. Nos. 5,596,988 and 4,889,407, each of which is incorporated by reference herein in its entirety.

In one aspect, the invention employs a chromophore-based IO biosensor having one or more sensing fibers implanted directly into patient tissue (e.g., the nervous system). In one embodiment, each fiber has a distal end reflector, such that light entering a proximal fiber end traverses the length of the fiber and returns, passing one or more times through a light-modulating detection or sensing portion. The detecting or sensing portion may be constituted by one or more regions of the fiber in which a bioactive chromophore is present; the chromophore changes color based on surrounding conditions, for example, by absorbing or binding to a particular analyte or measurand of interest (e.g., a neurotransmitter). The locally detected analyte thus alters the color or color saturation of return light from the fiber. Thus, the fiber sensor is configured to provide a spectral signature and intensity indicative of presence or concentration of the target analyte in the tissue surrounding the fiber. The controller unit connected to the fiber monitors the spectral characteristics of the return light in each fiber, and effects signal conditioning or processing to detect changing concentration and/or distribution in tissue of the target material, producing an output that controls the pump to initiate, adjust or terminate drug delivery in accordance therewith. One of ordinary skill in the art will also appreciate that other 10 biosensors, including fluorescence-based sensors, may be used in an analogous manner.

Preferably, the sensing and control regimen is effected substantially continuously to provide a closed loop feedback control. Moreover, the biosensor(s) may be selected or tailored to detect different relevant analytes depending on the treated condition.

The controller unit 20 can be of any conventional type that is able to accept signals from a sensor unit, such as an optical fiber based sensor. The controller unit may be appended to or incorporated within the infusion pump 12, or it may be a separate unit that is able to communicate control signals to the pump. The controller 20 should be capable of being programmed with one or more drug delivery regimens that will depend upon sensed biochemical parameters and events. Further, the controller unit 20 should be capable of being programmed after implantation within a subject, for example by telemetry. One of ordinary skill in the art will recognize that the controller preferably is one that is shielded or that is capable of being shielded so that it is not affected by environmental elements, such as RF energy. Further details of the controller unit 20 are provided below.

The controller unit 20 receives a signal from the sensor 16 that is indicative of a sensed biochemical parameter or event. Based on this data, the controller unit 20 provides a control signal to the pump assembly 12 to regulate delivery through catheter 14 in accordance with the output of the biosensor(s) 16. In this manner, drug delivery through the pump is able to closely track and immediately respond to the biochemical needs of a subject. This is unlike conventional therapies that If rely on secondary indicia such as changes in blood pressure or pH, or detection of ischemia or an electrical event. In the conventional therapies, a temporal or causal disconnect between deterioration or destabilization of a normal tissue state and the initiation or change of drug delivery may be introduced by the blood/brain barrier and/or by the complexity of the cellular processes involved or the physiological mechanics of drug delivery.

In a related aspect, the sensor signals may be processed or stored to provide a dose-response database that elucidates the ongoing cellular and metabolic mechanisms of drug response in the nervous system. The sensed values taken directly in the nervous system, for example, reflect immediate changes, or actual levels of drug response. The response characteristics may then be used to model appropriate pump control parameters for maintaining or stabilizing the desired cellular conditions in the nervous system, and the model may be constructed to avoid or minimize lag, delay and overshoot in the closed loop feedback control circuit.

Figure 2:
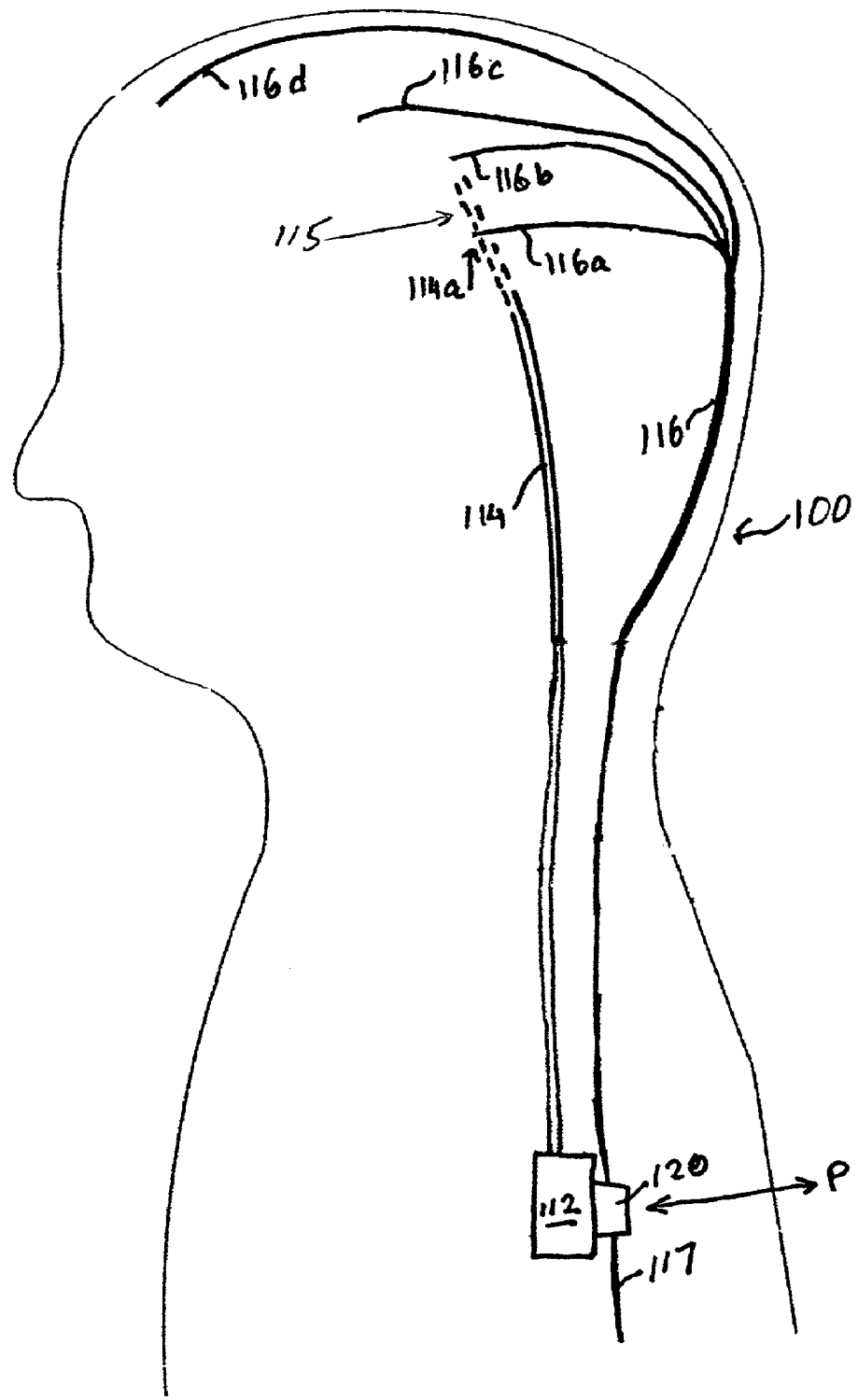
FIG. 2 illustrates a CNS embodiment of a system of the invention.

FIG. 2 illustrates another implantable closed-loop feedback control system 100 of the present invention, which includes a pump unit 112 as well as a delivery conduit assembly 114 having one or more ports or pore regions 114a located at a distal delivery end 115. In use, the delivery end 115 of the delivery conduit 114 is positioned in patient tissue (e.g., the brain) to deliver a drug thereto. A pump controller 120 is integral with or in communication with the pump 112, and the pump controller also communicates with a sensing component. The sensing component may be a biosensor array $116_i$ which, as shown, is adapted to be positioned in patient tissue. The biosensor array $116_i$ includes a plurality of sensors, where, in one example, sensor 116a is shown in the CSF, while other sensors 116b–116d are positioned in the brain in the general region of assembly 114. In various embodiments, related systems according to this aspect of the invention may employ a single sensor disposed in the CSF or the intrathecal space. This sensing modality is useful, for example, when the treatment drug is a small molecule or an electrolyte that disperses readily within the nervous system. Alternatively, the provision of multiple sensing elements $116_b$–$116_d$ may be employed in several other configurations to support different treatment modalities.

One such system places a plurality of biosensors in the form of optical fibers in the same tissue in which the delivery conduit is disposed, but at different angles around, or distances from the outlet of the delivery conduit. The sensing fibers then report the spatial distribution of the sensed material or state sensed. For example, the biosensors can gather data relating to the distribution and level of a drug such as dopamine in a region of the brain, or the distribution and concentration of a pain killer or chemotherapeutic agent delivered to a nerve region or to a localized tumor in the tissue. When used to map the distribution of the delivered drug or a metabolite thereof, the system is particularly useful for controlling delivery of large molecules (having exceptionally low transport rates in tissue) or small molecules (having high clearance rates from tissue) for drug protocols where predictive dosing or treatment models may vary greatly. In these circumstances, the provision of a direct measurement in the nervous system enables accurate dosing as well as accurate detection of tissue response.

Depending on the specific drug or treatment, systems of the invention may employ one or more biosensors positioned in CSF, as indicated by sensor 117 in FIG. 2, and deliver a drug to brain tissue. One of ordinary skill in the art will readily appreciate that such an arrangement may be altered so that the biosensors are present in brain tissue while drug is delivered intrathecally.

Another multi-sensor system of the invention may include sensors of different types, effective to measure several different metabolites, states or parameters. Multi-parameter control systems of this type may be particularly useful in trauma intervention, where the complex interaction of multiple, quickly changing parameters can potentially require delivery of different drugs or neuroprotectants to effectively stabilize and preserve brain tissue. They can also be used in cases where a neurological process depends on several materials, metabolites or neurological compounds, and the database must be accurately determined before the mechanism of operation or an appropriate model for drug intervention can be constructed.

Unless otherwise noted, the various components of the system illustrated in FIG. 2 can be the same as those described with respect to the system illustrated in FIG. 1.

Preferably, the controller units 20, 120 communicate with the sensors 16, 116 and include a data logging functionality for storing a matrix of data points representing the drug delivery rate of the pump and the material level or state detected by the sensors at different times. A hardware data port or transmitter, indicated schematically by arrow P (FIG. 2), may be provided to couple this data from the system to an external computer or storage system, where it may be stored and/or processed as a subject specific medical record, baseline report, or patient monitoring output. The database so transmitted may also be processed to determine suitable parameters for a drug delivery model, which is then used to control the delivery regimen, i.e., the controller response to changing sensor output values.

Thus, for example, based upon a physician's knowledge of a disease state, the dosage requirement for each measured (sensed) metabolite is established, and the physician then further determines the setting and any future adjustments based upon the database of information received from the sensor, or multi-sensor assembly or multi-parameter sensor assembly. As noted above, the sensors can be located not only locally (i.e., directly at the site of the event, disease or trauma), but also anywhere in the immediate area (thus sensing regionally) or remote from the site (in order to sense the "global" effect of a treatment regime).

In some embodiments the sensors 16, 116 are specifically designed to detect a particular event that is directly related the underlying disorder. For example, in the case of Parkinson's Disease, it is known that the nervous system uses the chemicals dopamine and acetylcholine to transmit signals that control muscle movements in the body. Dopamine is produced in the substantia nigra of the brain and is then sent to the striatum. Equal amounts of dopamine and acetylcholine in the striatum are essential for effecting smooth, coordinated muscle movement. Once in the striatum, these neurotransmitters are released and help direct muscle activity. Parkinson's Disease occurs when cells that produce dopamine die off. Without dopamine, the activity of other related brain areas can also be substantially altered. A drug delivery system of the present invention may be configured to treat Parkinson's Disease or related symptoms and address this condition by including a sensor for detecting low dopamine levels, or detecting a correlated brain tissue state. The controller then operates the pump to introduce to the striatum a drug, such as Levodopa, which the brain converts to dopamine. This direct stimulation/replacement regimen can alleviate symptoms of the disease in its early stage. The sensor assembly may detect levels of both dopamine and acetylcholine, sending the sensing signals to the controller, where governing parameters are set to trigger an automatic response. When concentrations of the infused drugs or sensed metabolites are too high or too low, the controller decreases or increases delivery of one or more drugs accordingly to maintain the desired relative and absolute levels. Systems for treating Parkinson's may also employ other dopamine agonists, e.g., Pramipexole, which has shown clinical efficacy in early stage treatment.

One type of sensor that may be useful in the application of the present invention to the treatment of Parkinson's Disease is a carbon-based microelectrode. Such carbon-based microelectrodes can detect a variety of chemical and biological species rapidly and with high specificity. The biomolecules that can be detected using this type of sensor include dopamine, glucose, and glutamate.

Another potential application of the system of the invention is in the detection of the presence of neurotoxins in the cerebrospinal fluid (CSF) or brain tissue in order to treat Adult Onset Dementia (AOD) of the Alzheimer's type. It is believed that some individuals with AOD of the Alzheimer's type have dysfunction with their resorptive mechanism, leading to the retention in the CSF of a substance which results in the formation of neurotoxins and/or histologic lesions associated with AOD of the Alzheimer's type. One example of such a substance is the protein beta A-4 amyloid. See, U.S. Pat. Nos. 5,980,480 and 6,264,625.

The system of the invention can be used to detect the undesirable elevated protein or peptide and deliver a counteragent/antagonist directly to a targeted site. Acetylcholinesterase inhibitors, which act to increase the concentration of acetylcholine, a brain chemical that helps nerve cells communicate, are a class of compounds that could be used to treat this condition. Examples of potentially useful acetylcholinesterase inhibitors include galantamine hydrobromide, tacrine hydrochloride, donepezil hydrochloride, and rivastigmine tartrate.

As applied to trauma events, systems of the invention may employ various antagonists to prevent cell death, or to block nervous system receptors that initiate or participate in the progression of an undesirable event, or to affect pathways or mechanisms so as to lower the metabolic rate and preserve viability of nervous system tissue. As such, systems of the invention are well adapted to carry out any of the previously proposed brain or nervous system treatment or intervention techniques with enhanced accuracy, response or effect.

The multi-parameter sensing embodiments of the invention may be configured to detect particular chemical characteristics and reactions of a particular living system or biological substance, using technology such as that illustrated in U.S. Pat. Nos. 5,596,988 and 4,889,407, and European Patent No. 745 220 B1. In this case, the controller would receive the detection signal generated by the sensor as a resulted analysis of a material or metabolite of interest and determine if the concentration is within a predetermined normal or non-critical range. The system may communicate with an external controller, e.g., telemetrically, to provide data to a treating physician.

The system of the invention can also be used to time drug delivery so as to optimize its effect in a patient. For example, drug delivery can be timed according to the Circadian rhythm. In some instances, this feature may offer a long-term survival advantage, for example, by timing drug delivery to minimize toxic side effects.

It is well known that the master clock in the mammalian brain is localized to the hypothalamic Id suprachiasmatic nuclei (SCN), acting in some ways as a "pacemaker." Circadian rhythms are internally generated rhythms in behavior and physiology with periods of about 24 hours. The 24-hour cycles that govern physiological and metabolic functions, enable organisms to follow the outside world's cues of light and dark. Awareness of underlying Circadian rhythmicity is essential for all pharmacological treatments. Researchers have targeted treatment strategies based on the following approaches: (1) boosting host immunity, (2) decreasing the body burden of drug metabolite toxicity, and (3) enhancing the cytotoxic effect of chemotherapeutic drugs. The coordination between cellular clocks in the brain and the rest of the body would enable the success of these treatment strategies.

By understanding which types of stimuli are able to phase shift the Circadian clock, one may be able to study the responses and understand the neural, pharmacological, and behavioral substrates of these different patterns of phase shifts. The system of the present invention may thus include an array of sensors which detect Circadian clock phase shifts induced by various neurotransmitters. An example would be the neurotransmitter Serotonin which is linked in many behaviors such as OCD (Obsessive Compulsive Disorder), Human mood disorders (depressions), and hunger. A patient's status with respect to the Circadian rhythm can also be tracked by providing sensors that detect, for example, Melatonin, an agent with powerful chronobiological properties.

In another embodiment optical sensors may be provided in a patient's eye to detect periods of daylight and darkness, thereby monitoring a patient's status with respect to the Circadian rhythm.

Drug delivery based on the Circadian Rhythm may be preprogrammed or it may be chemically or otherwise sensed based as described above.

Figure 3:
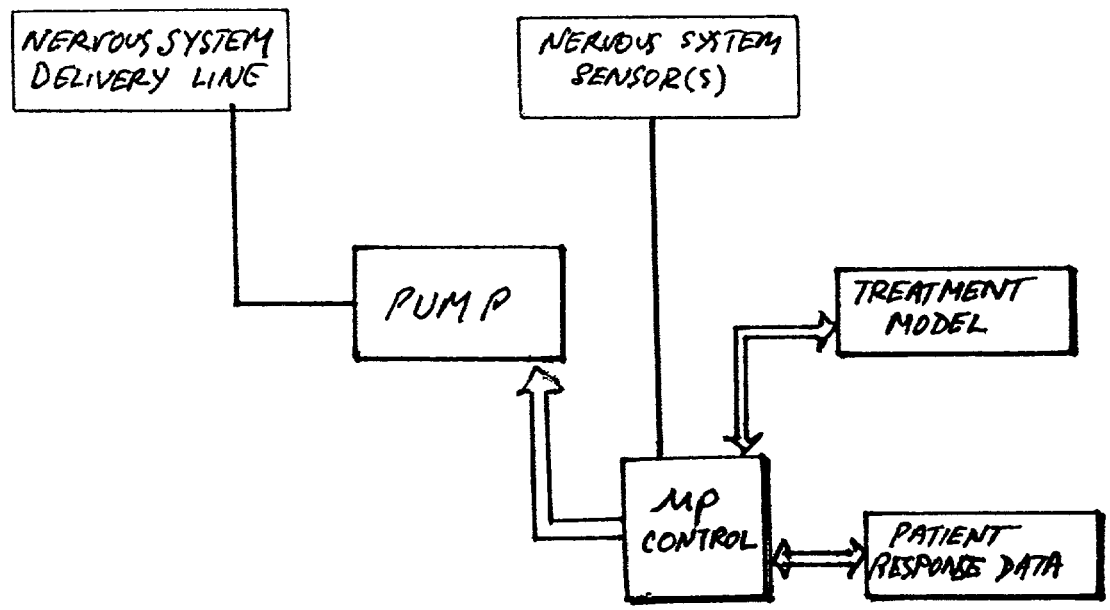
FIG. 3 illustrates a peripheral nervous system embodiment.

FIG. 3 illustrates method steps for carrying out the invention, in which an appropriate infusion pump, with an associated controller, is implanted in a subject and the delivery conduit is placed and directed to a desired tissue site (e.g., a part of the central nervous system). One or more sensors are likewise implanted in the subject at an appropriate site, local to or remote from the distal end of the delivery conduit and in the same or different tissue or organ system as the delivery conduit. Prior to implanting the pump, it is filled with a supply of drug or drugs to be delivered to a subject and the controller may be pre-programmed as appropriate. Once implanted the sensor operates to simultaneously detect and monitor certain biochemical and physiological conditions and events, and conveys a signal representative of such data to the controller. Based on this data, together with programmed operating instructions (which may be pre-programmed or programmed via telemetry at any time after implantation), the controller determines a dosing regimen to deliver the drug(s) to the subject as required by the physiological state of the patient at any given time. As a result of continuous monitoring of the biochemical state of the subject, drug(s) are delivered to the appropriate tissue site as needed to maintain the sensed physiological data within a predetermined range.

As shown, the method may alternatively or in addition operate to compile a database of patient-specific drug response data, thus establishing patient baseline conditions or elucidating the effect on each measured parameter of the delivered drug. This mode of operation may be used to correlate direct nervous system measurements with observed clinical behavior (e.g., muscular control in Parkinson's Disease), or with nervous system physiology (e.g., effective drug diffusion or clearance rates in tissue). It may also be used as the basis for determining a proper drug dose or pump control regimen for the detected parameters, i.e., to determine the treatment model.

In each case, the direct measurement and delivery in the nervous system is believed to offer a more effective, refined, and accurate procedure than existing systems.

The invention being thus disclosed and several illustrative embodiments described, modifications, variations and adaptations thereof will occur to those skilled in the art, and all such variations, modifications and adaptations are considered to be within the scope of the invention as defined herein and in the appended claims and equivalents thereof. All references disclosed herein are expressly incorporated herein by reference in their entirety.

What is claimed is:

1. A drug delivery system capable of delivering an effective amount of a drug to a subject, comprising:
   a delivery pump having a chamber capable of housing at least one drug;
   a delivery conduit connected to the pump and adapted to extend into a tissue site in the subject, the delivery conduit being effective to deliver the drug from a distal end thereof to the tissue site;
   a sensor, implantable within a subject, and capable of providing sensor output signals representative of sensed biochemical parameters; and a control unit in communication with the sensor and the pump and effective to compile and store a database of the sensor output signals, and to communicate a delivery signal that is continuously adjusted based on the database of sensor output signals to the pump to deliver the drug at a rate and for a duration effective to achieve a desired biochemical parameter within a predetermined range wherein both the delivery conduit and the sensor are adapted to be implanted in the central nervous system, and the sensor measures a biochemical parameter indicative of drug delivery.

2. The drug delivery system of claim 1, wherein the sensor includes an optical fiber, and the sensor output signal is a spectral output signal.

3. The drug delivery system of claim 1, wherein the sensor includes an electrochemical sensor, and the sensor output signal is an electrical signal or characteristic.

4. The drug delivery system of claim 1, wherein the drug is selected from among the group of drugs consisting of a pain killer, a chemotherapeutic agent, a neuroprotectant, a neurologically active material, an agonist to a neurologically active material, an antagonist to a neurologically active material, and combinations thereof.

5. The drug delivery system of claim 1, wherein the control unit comprises a processor operative to monitor and store dose-response information.

6. The drug delivery system of claim 1, wherein the sensor is implanted in the subject at a location remote from location of the distal end of the delivery conduit.

7. The drug delivery system of claim 1, wherein the delivery conduit is selected from the group consisting of a catheter, a needle, and a porous fiber.

8. The drug delivery system of claim 2, wherein the optical fiber is adapted to be implanted directly in nervous system tissue, and a portion of the optical fiber includes a bioactive chromophore effective to absorb or bind to an analyte of interest to alter color or saturation such that the return light from the fiber provides spectral data indicative of the local presence or concentration of the analyte of interest.

9. The drug delivery system of claim 8, wherein the analyte of interest is a neurotransmitter.

10. The drug delivery system of claim 2, wherein the sensor includes an array of optical fibers adapted to be implanted directly into nervous system tissue, such that the return light from the array of optical fibers provides spectral data locally indicating tissue distribution of a probed analyte or tissue state.

11. The drug delivery system of claim 1, wherein the sensor responds to a drug-related material selected from among the group consisting of a chemical, an ion, a biological molecule, a gas, and combinations or spectral indications thereof.

12. The drug delivery system of claim 2, wherein the sensor includes an enzyme immobilized at a sensing surface.

13. A method of drug treatment, comprising the steps of:

providing an infusion pump adapted to be implanted at a site in a subject, wherein the pump includes a housing having a chamber for containing one or more drugs and being operable to deliver the drug from the infusion pump;

providing a delivery pathway from the infusion pump to a target tissue site within the subject; and providing a sensor configured for implantation at a sensing location in the subject, wherein the sensor is adapted to detect a biochemical parameter or event at the sensing location and to produce an output signal indicative thereof; and providing a control unit, implantable at a site in a subject, wherein the control unit is able to receive the output signal from the sensor and wherein the control unit is in communication with the infusion pump;

wherein the control unit controls drug delivery from the infusion pump, responding to data provided by the output signal in a closed loop feedback cycle to regulate delivery of the drug from the infusion pump so as to release the drug at the target site to maintain the sensed biochemical parameter or event within a predetermined range; and wherein the control unit includes a processor and a memory, and the processor compiles and stores a database of sensed data and response data, and responds to the compiled and stored data to create and adjust a treatment model.

14. The method of claim 13, wherein the step of providing a sensor includes providing an optical or electrochemical sensor.

15. The method of claim 13, wherein the control unit is contained within or is separate from the infusion pump.

16. The method of claim 15, wherein drug delivery is timed to synchronize with periods within the subject's Circadian Rhythm.

17. The method of claim 16, wherein drug delivery is preprogrammed to synchronize with periods within the subject's Circadian Rhythm.

18. A method for delivering an effective amount of a drug to a subject, comprising:

sensing one or more biochemical parameters related to the central nervous system of a subject in response to the delivery of a drug to produce sensed signals;

creating a dose-response database from the sensed signals;

modeling appropriate pump control parameters for maintaining desired conditions based on the dose-response database;

delivering a drug to a subject from a drug delivering pump operated under the appropriate pump control parameters; and repeating the step of sensing one or more biochemical parameters to modify the dose-response database and to model appropriate pump control parameters.

* * * * *